United States Patent [19]
Duce et al.

[11] Patent Number: 6,063,249
[45] Date of Patent: May 16, 2000

[54] OXYGEN SENSOR

[75] Inventors: Richard William Duce, Flushing; Richard Courtney Kuisell, Lapeer, both of Mich.

[73] Assignee: General Motors Corporation, Detroit, Mich.

[21] Appl. No.: 09/076,696

[22] Filed: May 12, 1998

[51] Int. Cl.[7] .................................................. G01N 27/407
[52] U.S. Cl. .......................... 204/424; 204/426; 248/511; 248/523
[58] Field of Search .................... 204/421–429; 248/511, 518, 523

[56] References Cited

U.S. PATENT DOCUMENTS 5,817,920 10/1998 Kuisell et al. ........................ 204/424
5,886,248 3/1999 Paulus et al. ........................ 204/426

*Primary Examiner*—T. Tung
*Attorney, Agent, or Firm*—Vincent A. Cichosz

[57] ABSTRACT

An oxygen sensor includes an elongated planar sensing element and a lower insulator sealably mounted within a tubular shield. The sensing element extends through a central opening disposed in the lower insulator into a sensing chamber. An annular glass support bonded at an end of the insulator is in non-bonding contact with the sensing end of the sensing element. A portion of the sensing element adjacent the glass support is coated with a carbon-based ink to prevent bonding of the glass support to the sensing element. In an alternative, a metal foil support may extend between the sensing element and the glass support. The metal support includes a plurality of dimples disposed on opposing walls that extend inwardly to contact and non-bindingly support the sensing element therein.

6 Claims, 2 Drawing Sheets

OXYGEN SENSOR

TECHNICAL FIELD

The present invention relates generally to oxygen sensors. More particularly, the present invention relates to a support for maintaining a sensing element of an oxygen sensor.

BACKGROUND OF THE INVENTION

Exhaust oxygen sensors have been used for many years in automotive vehicles to sense the presence of oxygen in exhaust gasses, for example, to sense when an exhaust gas content switches from rich to lean or lean to rich. One known type of oxygen sensor includes a flat plate oxygen sensor formed of various layers of ceramic and electrolyte materials laminated and sintered together with electrical circuit and sensor traces placed between the layers in a known manner.

Because automotive oxygen sensors are mounted to members of the vehicle exhaust flow system, the sensors must be durable, able to withstand vibration and jarring such as would occur during installation and normal vehicle operation and able to withstand shock from the occasional stone or other small road debris that may happen to be thrown at the sensor, for example, by the vehicle's tires.

SUMMARY OF THE INVENTION

It is an object of this invention to provide an oxygen sensor according to claim 1.

Advantageously this invention provides an oxygen sensor for use in an automotive vehicle exhaust system with improved durability.

Advantageously, this invention provides an oxygen sensor suitable for use in a motor vehicle with improved resistance to mechanical shock and more robustness for a rugged vehicle environment.

Advantageously, this invention provides an oxygen sensor with non-binding support of the sensing end of an oxygen sensing element which prevents lateral movement of the sensing element to reduce mechanical stresses (i.e., shock and vibration), but permits longitudinal movement of the sensing device which reduces mechanical stress associated with differences of thermal expansion between the components during operation.

Advantageously, this invention provides an oxygen sensor with a non-binding support for an oxygen sensing element that provides improved resistance to failures caused by thermal shock exposures.

BRIEF DESCRIPTION OF THE DRAWINGS

The present invention will now be described by way of example with reference to the following Figures, in which.

DETAILED DESCRIPTION OF THE INVENTION

Figure 1:
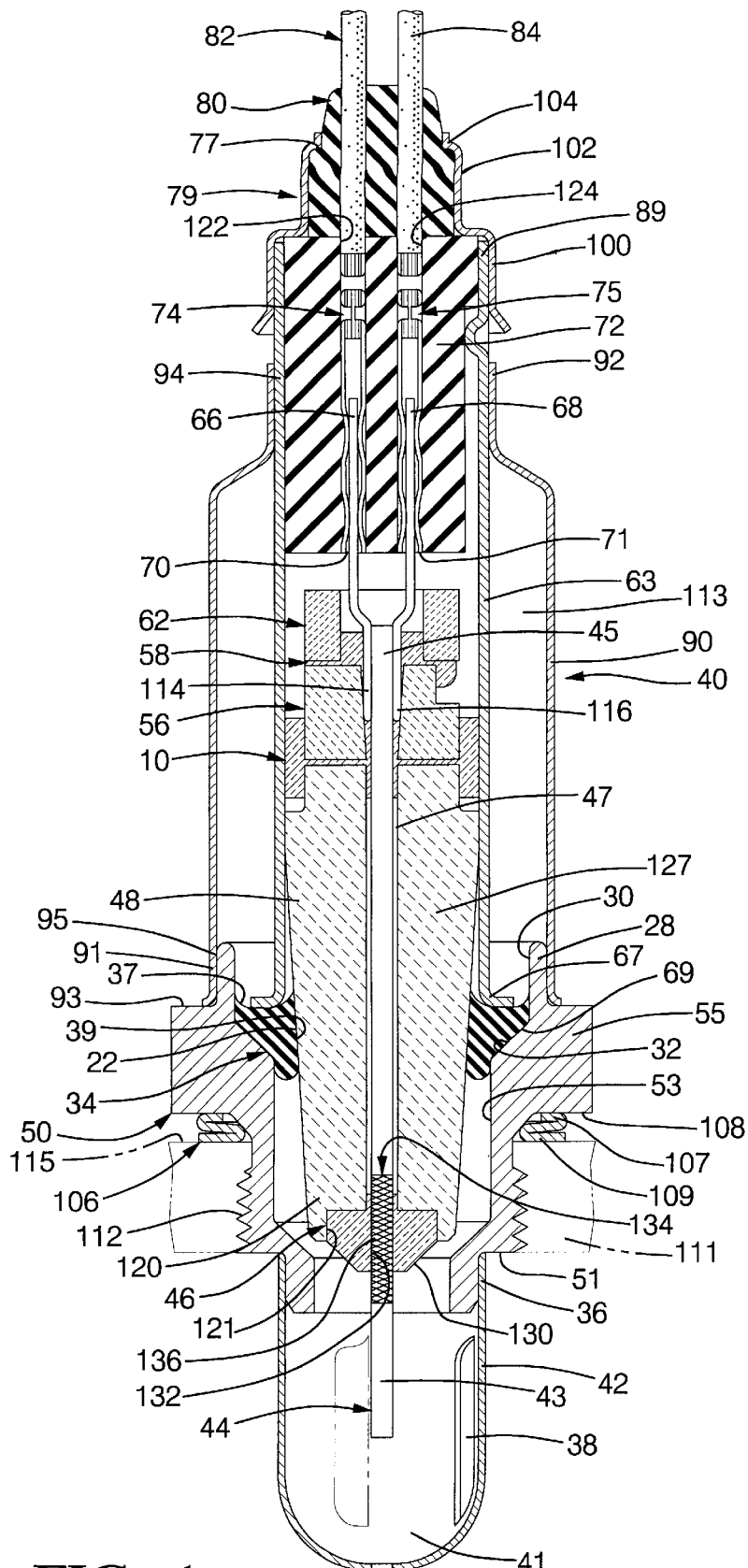
FIG. 1 illustrates a cross-sectional view of an example oxygen sensor according to this invention.

Referring now to FIG. 1, the example oxygen sensor 40 shown includes a housing structure generally formed of upper shield 63, lower shield 42, outer shield 90 and shell 50. Terminal adapter 72, upper insulator 62, wedge ring 56, lower insulator 48 and a portion of sensing element 44 are located within the upper shield 63. The sensing element 44 is an exhaust oxygen sensing element of a known type with a generally flat elongated rectangular shape. A first end 43 of sensing element 44 includes an oxygen-responsive structure fabricated into the sensing element 44 in a known manner, preferably along with a heater of a known type. At the opposite end 45 of the sensing element 44, the lower ends 114 and 116 of terminals 66 and 68 contact external pads (not shown) on the end 45 to provide electrical connection between the female terminals 74 and 75 and the sensing element 44. The ends 114 and 116 of the terminals 66 and 68 are maintained against the end 45 of the sensing element 44 by a wedge ring 56 having an internal wedged shaped opening pressed against the ends 114 and 116 forcing them in place against the terminal pads on end 45 of sensing element 44.

An upper insulator 62 is maintained in place above the wedge ring by glass support 58. Below the wedge ring 56, a lower insulator 48, that acts as a thermal and electrical insulator as well as a support member, extends from close to the wedge ring 56 to the sensing chamber 41 where end 43 of the sensing element 44 is located. A glass seal 10 supports the sensing element 44 within upper shield 63 and provides sealing engagement between the sensing element 44 and upper shield 63, forming a gas-tight barrier between the sensing element ends 43 and 45.

The glass seal 10 has a flat circular disk portion, including a centrally located rectangular opening in which the planar sensing element 44 is located. At an outer radial periphery of the flat disk portion, the seal forms a circular cylindrical wall extending axially away from the flat circular disk portion in first and second directions opposite to each other. The outer periphery of the circular cylindrical wall engages and bonds with the inner cylindrical wall of the upper shield 63 and the inner periphery of the circular cylindrical wall engages and bonds with the wedge ring 56 and the lower insulator 48, as do the top and bottom planar surfaces of the flat disk portion. The rectangular opening engages and bonds to the planar sensing element 44. When the assembly shown is heated to melt and bond the glass seal, glass flow and capillary action draw the glass between the sensing element 44 and the inner openings of the wedge ring 56 and the lower insulator 48. An example suitable glass seal 10 is described in pending patent application Ser. No. 08/600,136, having a disclosure incorporated herein by reference.

The lower insulator 48 has a central opening 47 through which the sensing element 44 passes. The sensing element 44 is supported near the sensing end 43 by a glass support 46 bonded to the lower end 120 of the lower insulator 48 within recess 121. The glass support 46 is a annular disk having a frusticonical lower surface 130 and a central rectangular bore 132 to receive the sensing end 43 of the sensing element 44.

In accordance with the present invention, a portion 134 of the sensing element 44 is covered with a thin coating or ink 136 comprising a carbon-based material, such as graphite. The ink 136 is coated on all sides of the sensing element 44 over at least the portion 134 of the sensing element that is expected to contact the glass support 46 after the heating and melting of the glass support. The carbon-based ink 136 functions to provide a barrier layer to prevent bonding or wetting of the glass support 46 to the ceramic sensing element 44. When the assembly is heated to melt and bond the glass to the lower insulator 48, the glass flow and capillary action draw the glass between the coated portion 134 on the sensing element 44 and the inner opening 47 of the lower insulator 48.

In an alternative embodiment, the ink 136 may be replaced by a sleeve or thin metal sheet wrapped around the sensing element 44 to provide the barrier layer necessary to prevent bonding of the glass support to the sensing element.

The non-binding characteristics of the ink 136 and sleeve permit the glass support 46 to be in intimate contact with the end 43 of the sensing element 44 to provide support from mechanical stresses, such as shock and vibration but, permit the sensing element to move or expand longitudinally which reduces stresses caused by differences of the thermal expansion of the components during operation. The reduction of this excess stress attributed to thermal expansion differences improves the ability of the oxygen sensor 40 to survive impact and vibration loads caused by drops and other mechanical stresses.

Figure 2:
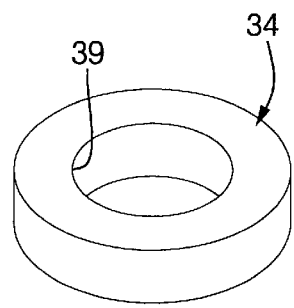
FIG. 2 illustrates a perspective view of an example gasket for use with the oxygen sensor shown in FIG. 1.

In the example shown, the lower end 67 of the upper shield 63 extends to a middle portion 127 of the lower insulator 48 so that the lower end 120 of lower insulator 48 extends out from the upper shield 63. The shell 50 has an inner cylindrical opening 53 wide enough to accommodate passage of the lower insulator 48 without direct contact between the shell 50 and the lower insulator 48. End 67 of the upper shield 63 is seated sealingly in the annular depression 37 formed in gasket 34 by compression that occurs during assembly. More particularly, before assembly, the gasket 34 has the shape shown in FIG. 2. Because the gasket, in the preferred example, is formed of a ceramic fibrous material bonded by a vermiculite material of a known type such as used for matting in catalytic converter assemblies, the gasket 34 deforms in response to the compression forces between the lower end 67 of upper shield 63 and the cylindrical and conical inner surfaces 30 and 32 of the shell 50 to take on the shape shown in FIG. 1. Additionally, the outer surface 22 of the lower insulator 48 forms a wedge shape, with the wide end of the wedge proximate to seal 10 and the narrow end 120 proximate to the sensing chamber 41. The wedge shape provides radially outward compressive forces between the lower insulator 48 and the shell 50 so that the gasket 34 is compressed radially outwardly from surface 39. As is shown in FIG. 1, the lower end 67 of the upper shield 63 is preferably flared out to provide a compressing surface against gasket 34. Through the compressive forces, the gasket 34 provides gas-resistant sealing and compliant (non-rigid) supporting engagement to the upper shield 63 and to the shell 50. The conical surface 32 orients the surface 69 of the gasket 34 into the preferred direction for thermal expansion of gasket 34.

The shell 50 includes a body portion 55 and threaded portion 112. The body portion 55 is shaped to accommodate a wrench or other tool 5 for tightening the threaded portion 112 into a mount welded to an exhaust pipe or other component of an exhaust flow system, enabling the sensor chamber 41 to be located within a flow of exhaust gasses to be measured. An annular gasket 106 has a first axial end 107 that rests against shoulder 108 of the body portion 55 of the shell 50 and a second axial end 109 that rests against the surface 115 of the mount 111 when the shell 50 is threadably engaged thereto.

The lower shield 42 defines the chamber 41 and includes a plurality of vents 38 for allowing passage of exhaust gas into and out of the chamber 41 so that the gasses may be sensed by the sensing element 44. An open end 36 of the lower shield 42 is mounted against the shoulder 51 of the shell 50 and may be welded in place or held in place by a secure friction fit.

At the upper end of the upper shield 63, the terminals 66 and 68 engage female terminal slots 70 and 71 of the terminals 74 and 75, which are connected to the electrical wires 82 and 84 in a known manner. The terminals 74 and 75 are tightly fit in the cylindrical openings 122, 124 passing through the terminal adapter 72. The wires 82 and 84 pass through the cable seal 80, generally comprising a rubber material suitable for use in a high temperature environment, and extend into the passages 122, 124 of the terminal adapter 72. The seal 80 is maintained in place by the metal retainer 79 having an end 104 forming a seat around the shoulder 77 of the seal 80, a central portion 102 around the lower portion of the seal 80 and a lower end 100 forming a cylindrical opening tightly fit around the upper end 89 of the upper shield 63. The retainer 79 is preferably welded or otherwise secured in a leak-proof manner to the upper end 89 of the upper shield 63.

The outer shield 90 has an upper end 92 of reduced diameter to provide a tight fit around the outer surface of the portion 94 of the upper shield 63 and is held in place by either a weld, braze or a tight friction fit. The body of the outer shield 90 is expanded radially outward from the upper shield 63 providing an annular space 113 between the upper shield 63 and the outer shield 90. The lower end 91 of the protective shield 90 fits around the outer cylindrical surface 95 of the extending end 28 of the shell 50 and abuts against seat 93. Lower end 91 of the protective shield 90 fits around the outer cylindrical surface 95 of the extending end 28 of the shell 50 and abuts against seat 93. Lower end 91 is held in place by either a tight friction fit or a weld. If desired, a packing material may be placed around the lower portion of the upper shield 63 and the outer shield 90. The packing material, for example a packed wire mesh or other compliant material, may serve to provide added support if necessary or desirable. Because the outer shield 90 is affixed to both the upper shield 63 and the shell 50, the outer shield 90 mechanically holds the upper shield 63, the gasket 34 and the shell 50 in compressive force engagement.

For the structure shown in FIG. 1, example material for the shields 42, 63 and 90 and for the shell 50 is high chrome or high nickel stainless steel, all steels chosen for high temperature endurance, high-strength and corrosion resistance. The terminal adapter 72 may be a plastic or ceramic durable in the high temperature environments to which oxygen sensors are exposed and the upper insulator 62, wedge ring 56 and lower insulator 48 may comprise steatite, alumina, ceramic or other suitable high temperature material providing the desired support, strength and thermal and electrical insulating properties described herein. The glass seal 10 preferably is formed of glass having a melting temperature higher than the expected operating temperature of the sensor at the region of the glass seal 10 and having a coefficient of thermal expansion appropriate to maintain the gas tight seal with the upper shield 63.

In assembly of the upper and lower insulators 62 and 48, the wedge ring 56, the glass supports 58 and 46 and the glass seal 10 are located within the upper shield 63 in their respective relative positions as shown in FIG. 1 and are placed in an oven where they are brought to a temperature higher than the melting temperature of the glass, allowing the glass to flow into sealing and bonding contact with the respective members shown. The oven is then controllably cooled so that the glass becomes more solid to provide the structural and sealing properties described herein. The rest of the sensor is then assembled to take the structure shown.

The annular gasket 34 preferably comprises a high temperature durable fibrous materials, such as a ceramic fiber material, bonded together by a vermiculite or other suitable bonding material. In the preferred example, the vermiculite bonding material is of a known type, for example, used as support matting in catalytic converter assemblies, that expands when heated to maintain a sealing function between the shell 50 and gasket 34 and between the gasket 34 and lower end 67 of upper shield 63, thus maintaining the seal over all operating temperatures of the sensor 40.

In alternative examples, the gasket 34 may be made of other compliant support materials such as wire mesh, which would be used if the gas-resistant sealing function is not paramount. The gasket 34 may also be a high temperature spring material that may or may be used in conjunction with a sealing material, depending whether the sealing function is thought necessary in the particular example.

As can be seen, there is no direct non-compliant or non-deformable mounting between the upper shield 63 and the shell 50 or between the lower insulator 48 and the shell 50. Instead, the mounting contact to the shield 63 and its internal components is made vis-à-vis the gasket 34 at the lower end 67 of the upper shield 63 and vis-à-vis the protective shield 90 at the area 94 near the upper end 89 of the upper shield 63. This configuration has been found to reduce the potential for mechanical shock, traveling from the protective shield 90 or the shell 50 to the components internal of the upper shield 63. Of most particular relevance is the glass seal 10, which, when implemented with the structure shown, maintains valid mounting support and sealing functions through severe shock and drop tests demonstrating an overall robustness to the design shown.

Figure 3:
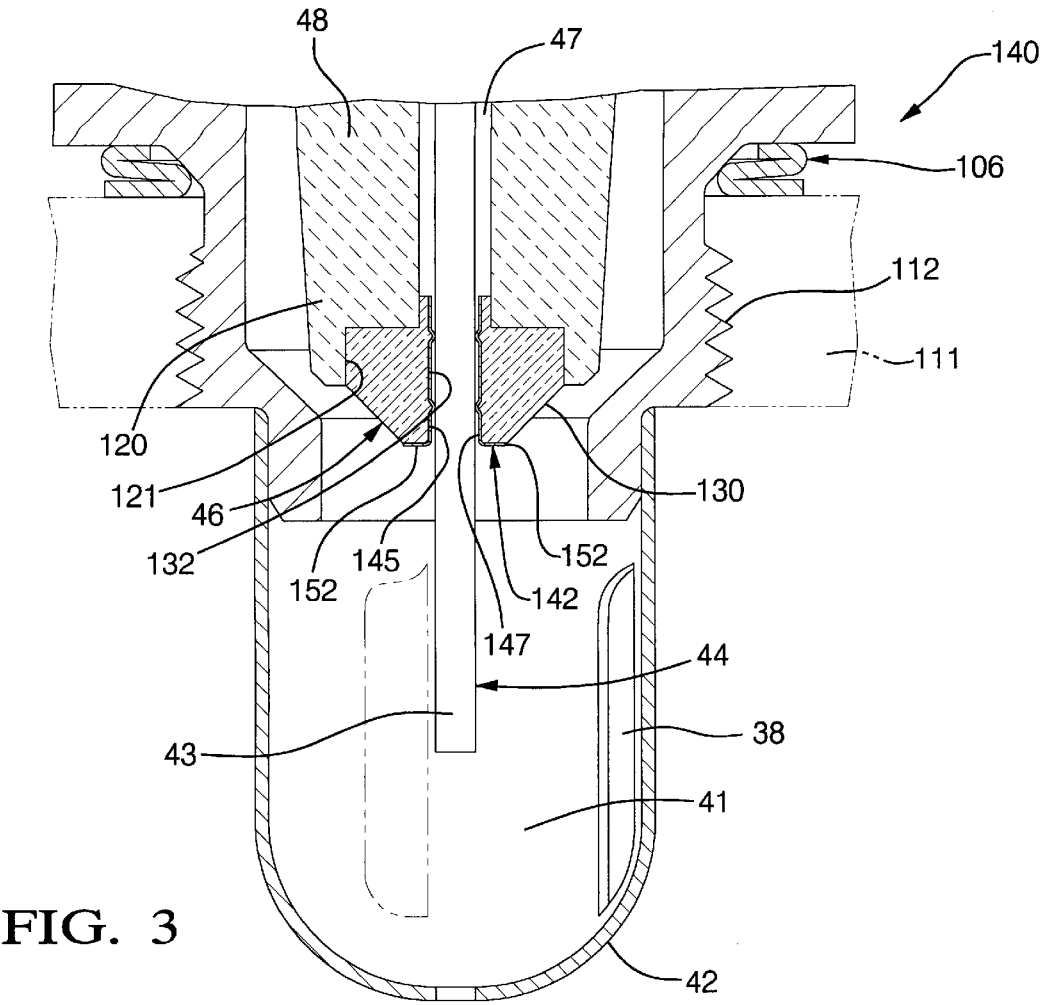
FIG. 3 illustrates a cross-sectional view of a portion of a second example oxygen sensor according to this invention.

Referring now to FIG. 3, the example oxygen sensor 140 shown is similar to the oxygen sensor 40 shown in FIG. 1 and like parts are labeled with like reference numerals. The sensor 140 differs from sensor 40 in FIG. 1 in that carbon-based coating 134 in FIG. 1 is now replaced by a metal foil support 142 best shown in FIG. 4. The metal foil support 142 provides a resilient support for the sensing element 44, and functions as a barrier to prevent bonding of the glass support 46 to the sensing element when the glass support is bonded to the lower insulator 48.

Figure 4:
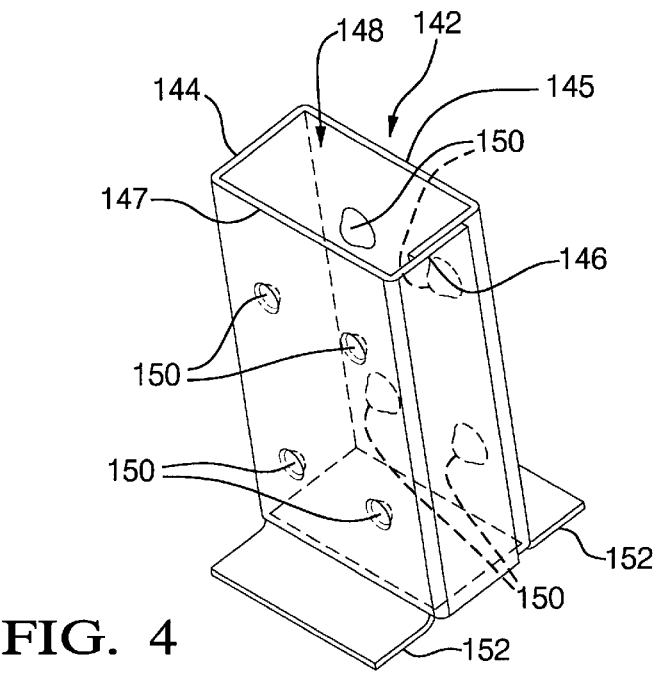
FIG. 4 illustrates a perspective view of a metal foil support shown in FIG. 3.

Referring also to FIG. 4, the metal foil support 142 is formed of a single sheet of foil that is folded to form a rectangular support having sides 144–147 that define a rectangular channel 148 for receiving and supporting the sensing end 43 of the sensing element 44. Opposing side walls 145, 147 include a plurality of dimples 150 extending inwardly to provide resilient support to opposing planar surfaces of the sensing element 44.

The metal support 142 extends into the central bore 132 of the glass support 46 and the central opening 47 of the lower insulator 48, wherein end shoulders 152 abut the lower end of the glass support to ensure proper positioning of the metal support therein. It is necessary for the metal support 142 to extend sufficiently into the central opening 47 of the lower insulator 48 to prevent the glass support 46 from bonding to the sensing element 44 due to the capillary action of the glass when melted. The glass support is bonded to the lower insulator 48 and the metal foil support 142 by heating the glass to its melting point and then controllably cooling the glass.

Similar to the oxygen sensor 40 in FIG. 1, the combination of the glass support 46 and the metal foil support 142 improves shock resistance of the sensor 140, and allows for different thermal rates of expansion between the end 43 of the sensing element 44, the glass support 46 and the lower insulator 48.

What is claimed is:

1. An oxygen sensor comprising:

an elongated sensing element having an oxygen-responsive first end;

a housing;

a glass support;

a coating disposed on a portion of the sensing element adjacent the glass support, whereby the coating prevents bonding of the sensing element to the glass support; and said elongated sensing element supported within said housing by said glass support, wherein said elongated sensing element is in non-bonding contact with said glass support.

2. The oxygen sensor defined in claim 1 wherein the coating is formed of carbon-based material.

3. An oxygen sensor comprising:

an elongated sensing element having an oxygen-responsive first end;

a housing;

a glass support;

a sleeve disposed on a portion of the sensing element adjacent the glass support, whereby the sleeve prevents bonding of the sensing element to the glass support; and said elongated sensing element supported within said housing by said glass support, wherein said elongated sensing element is in non-bonding contact with said glass support.

4. The oxygen sensor defined in claim 3 wherein the sleeve is formed of metal foil.

5. An oxygen sensor comprising:

an elongated sensing element having an oxygen-responsive first end;

a housing;

a glass support;

a second support disposed around a portion of the sensing element adjacent the glass support, the second support including opposing walls having a plurality of dimples extending inwardly for contacting the sensing element, whereby the second support prevents bonding of the sensing element to the glass support; and said elongated sensing element supported within said housing by said glass support, wherein said elongated sensing element is in non-bonding contact with said glass support.

6. The oxygen sensor of claim 5 wherein the second support further comprises end shoulders for engaging the insulator to properly locate the second support about the sensing element.

* * * * *